United States Patent [19]
Adams

[11] Patent Number: 5,800,346
[45] Date of Patent: Sep. 1, 1998

[54] SURGICAL RETRACTOR HOLDER

[76] Inventor: Carlton Z. Adams, 1712 Woodacre Ct., Carmichael, Calif. 95608

[21] Appl. No.: 942,699

[22] Filed: Sep. 30, 1997

[51] Int. Cl.$^6$ .................................................. A61B 17/00
[52] U.S. Cl. .................................................. 600/227; 600/201
[58] Field of Search .................................. 600/206, 227, 600/201; 128/849, 851, 852

[56] References Cited

U.S. PATENT DOCUMENTS

| | | |
|---|---|---|
| 2,493,598 | 1/1950 | Rozek . |
| 4,596,245 | 6/1986 | Morris ................................ 128/852 |
| 5,709,220 | 1/1998 | Kellan ................................ 128/852 |

Primary Examiner—Jeffrey A. Smith
Attorney, Agent, or Firm—Bacon & Thomas

[57] ABSTRACT

A surgical retractor holder includes a length of pliant material having opposed fastening end areas at which hook elements or the like are located for engaging opposite sides of a surgical table. Open ended pockets are provided along the length of the material for receiving the proximal end of a retractor handle to secure the handle in position when the length of material is fixedly secured to a surgical table across a surgery patient. The retractor holder enables the retractor to be secured in position without the need for manipulation by a surgical assistant.

7 Claims, 1 Drawing Sheet

SURGICAL RETRACTOR HOLDER

BACKGROUND OF THE INVENTION

1. Field of the Invention

This invention relates to a belt-like holder for maintaining a surgical retractor or clamp in place during a surgical procedure.

2. Related Art

Retractors and clamps of various kinds are commonly used in surgical procedures wherein the retractor or clamp is positioned within the cavity of a surgery patient so as to position or locate a member or organ of the body of the patient at a desired location to enable a surgeon to obtain free access to a portion of the body or body cavity during a surgical procedure. For convenience, surgical retractors, clamps and the like having some form of manipulating handle will all collectively be referred to herein as "retractors."

Typically, one or more surgical assistants inserts a retractor or retractors into an opening surgically created in the body of a patient and then holds the retractor(s) in place while the surgeon carries out the surgical procedure. The need for such surgical assistance increases the cost of the surgical procedure and the presence of the assistant in the operating field requires the surgeon to avoid the hands and arms of the assistant or assistants that are holding the retractor in position during the surgical procedure.

U.S. Pat. No. 2,493,598 granted to Rozek on Jan. 3, 1950, shows a self-retaining retractor device utilizing adjustable belt elements and integrated retractors for holding the edge areas of a surgical opening in extended position to enable a surgeon to access the opening without interference and without requiring an assistant.

It has been recognized that the need to provide an assistant during surgery to hold or retain a retractor increases the cost of a medical procedure where an assistant would not otherwise be required. The present invention intends to overcome the disadvantages associated with using assistant personnel during surgical procedures for holding a retractor in place during a surgical procedure.

BRIEF SUMMARY OF THE INVENTION

This invention comprises a surgical belt-like retractor holder constituted of a length of pliant material having opposed fastening end areas located along the material length to which are secured hook elements or the like for engaging opposed sides of a surgical table. The pliant material includes open ended pockets along its length that are arranged to receive the proximal handle end of a retractor device to secure the handle at a fixed location during a surgical procedure after the material has been secured over the body of a patient and to the side areas of a surgical table.

The material is adjustable in length and the pockets are preferably closed at one end so that a handle of a retractor is securely retained in position relatively to a surgical table and a patient during a surgical procedure.

The retractor holder is constructed of inexpensive materials and formed using low cost procedures so that the cost of the holder, which is intended to be utilized only a single time, is kept to a minimum.

BRIEF DESCRIPTION OF THE DRAWINGS

With reference to the appended drawings.

DETAILED DESCRIPTION OF THE PREFERRED EMBODIMENTS OF THE INVENTION

Figure 1:
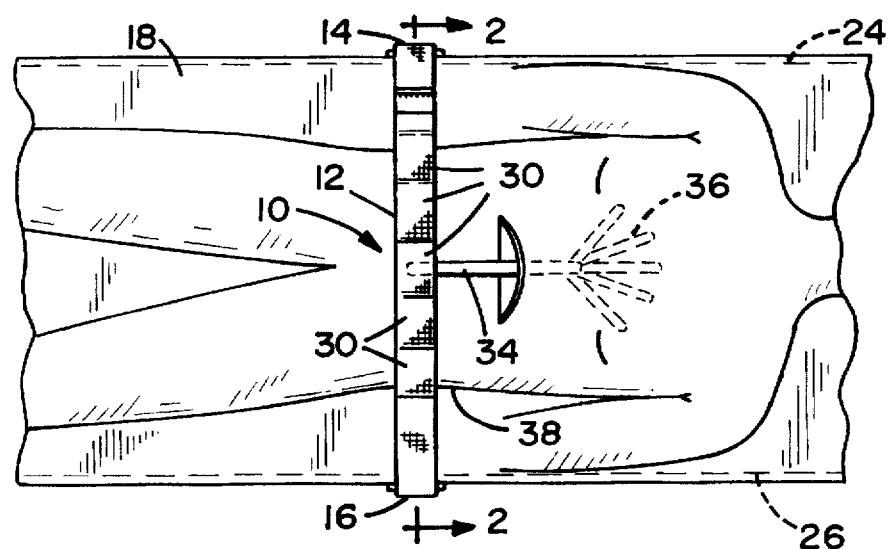
FIG. 1 shows schematically a preferred embodiment of a surgical retractor holder made in accordance with the invention during use.
Figure 2:
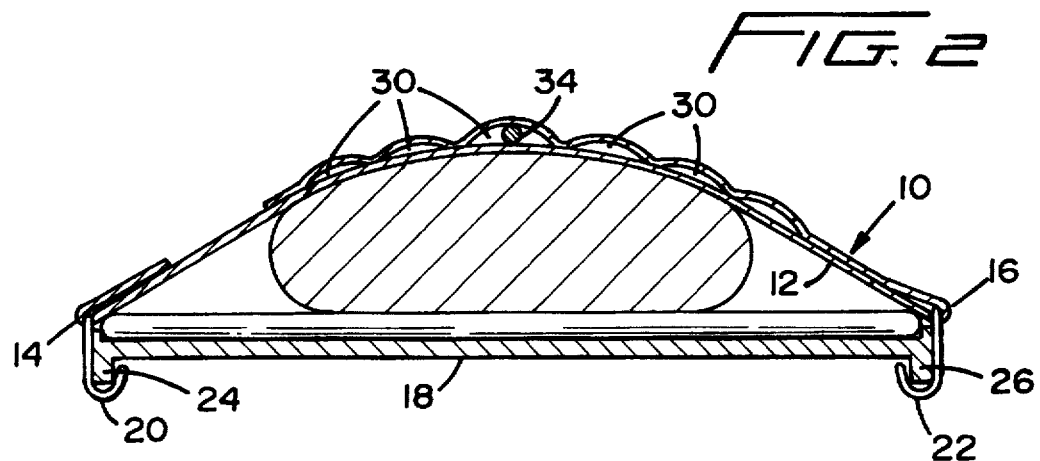
FIG. 2 is a section view taken along line 2—2 in FIG. 1.

With reference to the appended drawings, a surgical retractor holder 10 is formed of a length of pliant material that preferably is relatively inextensible during use and having opposed fastening end areas 14, 16 located along the material length.

To enable the opposed fastening end areas to be secured to a surgical table 18, surgical table engaging hook elements 20,22 are provided at the fastening end areas of the material 12 so that the hooks can be located beneath the typical surgical table rails 24, 26 customarily provided along either side of the lower side areas of a surgical table.

Preferably, one of the hooks 22 may be fixedly connected to one fastening end area 16 of the material 12 while the opposed hook element 20 may be adjustably fastened to the opposite fastening end area of the material 12, for example, by threading a loop 28 of the material 12 through a ring provided in a hook element 20, the loop being fastened with respect to the length of material 12 by an appropriate fastener element or elements that prevent reverse loosening movement of the loop 28 through the ring provided in hook element 20.

For example, the loop 28 may be secured to the length of material 12 by conventional loop and hook fastener elements marketed under the trademark VELCRO, or other appropriate fasteners, including clips, snaps, buckles, buttons and the like. By adjusting the loop 28 relative to the hook 20, the effective length of material 12 between the opposed fastening end areas 14, 16 can be varied to tension the material length in position in a manner to be described below.

The material 12 may have a surface texture capable of functioning as a multiple loop type material of a conventional loop and hook type fastener and a hook type fastener material comprising a multiple loop type material of the type associated with conventional multiple loop and hook type fasteners may be attached to the material length adjacent one fastening end area so that, after threading of the loop material through the ring, the loop type fastening material may be directly secured to the textured surface of the material 12 to prevent reverse loosening motion of the material 12 through the hook 20.

Figure 3:
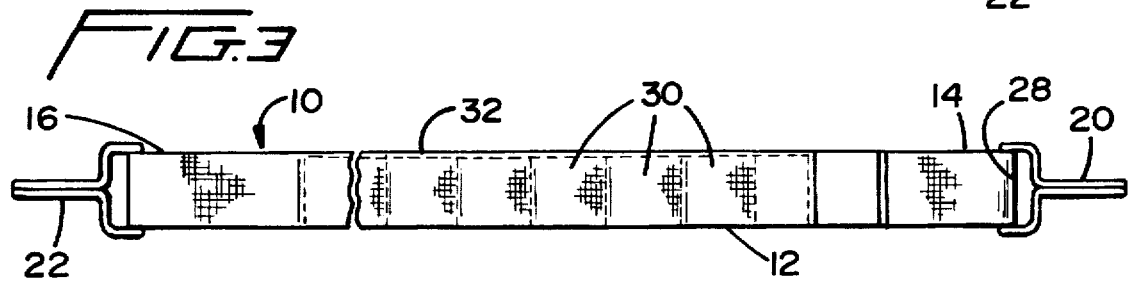
FIG. 3 is a top plan view of the retractor holder shown in FIG. 1.
Figure 4:
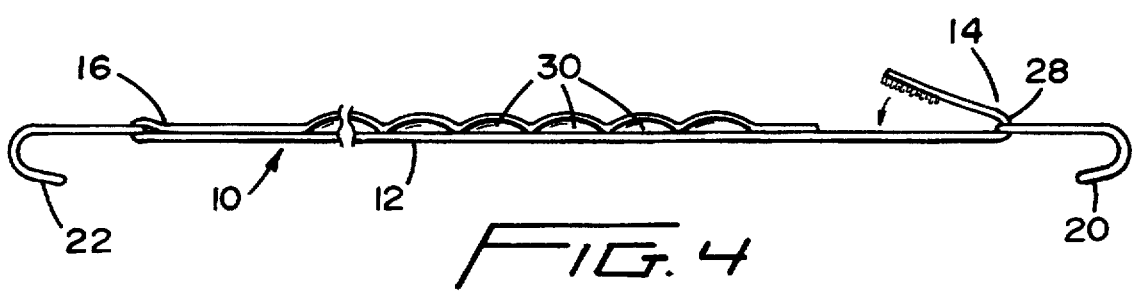
FIG. 4 is a side elevation view thereof.

Located along the length of the material 12 are provided pockets 30 that include an open end facing in the same direction transversely of the length of the material 12. While the pockets may be open at opposed ends, preferably the pockets are closed at their ends opposite to the open ends, as illustrated at 32. The pockets may be formed by simply looping the material 12 at forward end 16 through a ring provided in hook 22, as shown in FIGS. 3 and 4 and periodically fastening the loop of material 12 to itself along the underside of the material length 12. Alternatively, a separate length of material may be secured to the underside of the material 12 to provide the open ended pockets 30. If desired, the pockets 30 could be formed on the upper side of material 12. Any number of different arrangements can be utilized to provide the open ended pockets 30 along the length of the material 12 and the invention is not intended to be limited by any specific means for providing the open ended pockets 30. Stitching, adhesive, or separate fasteners may be utilized to create the open ended pockets, without limitation. While only a single fastener end area 14 is shown as being adjustably secured to a hook 20, it is to be understood that both ends of the material 12 may be adjustably connected to the hook elements 20, 22.

Hook elements 20, 22 may be made of shaped metal, plastic or other materials suitable for the purpose of securing the opposed end areas of the material 12 to a surgical table along rail elements 24, 26 commonly provided along such tables or other elements that will restrain the movement of the fastening end areas of the material 12 in position relative to a surgical table 18.

The material 12 may be woven fabric, non-woven fabric-like material, plastic or natural (e.g. leather) sheet material, coated or uncoated materials, or other appropriate strap-like material that can be tensioned in position on a surgical table overlying a patient upon whom a surgical procedure is to be performed.

In use, the holder 10 is intended to retain the manipulating end or handle 34 of a surgical retractor, for example, a fan-type retractor 36 that may be placed in a body cavity of a surgery patient to support or position a body member or organ at a desired location during a surgical procedure adjacent the retractor.

Normally, an assistant to the surgeon manipulates the retractor in position and then holds it in the desired location during the surgical procedure. This requires the presence of another person in the immediate field of the procedure, as well as additional hands or hand of the assistant in the surgical field.

In accordance with the present invention, the surgeon or an assistant hooks a length of the material 12 at opposed ends to the surgical table 18, for example, by utilizing hooks 20, 22, engaging rails 24, 26 beneath the surgical table 18, with the central portion of the material 12 extending over the patient 38. The material 12 is located so that the open ends of the pockets 30 extend toward the handle 34 of retractor 36 and the belt is tightly secured in place over the patient 38. The retractor 36 is then positioned in the body cavity at the desired location or close to the desired location and is manipulated so that the proximal end of the handle 34 is located in the open end of a pocket 30. If desired, the material 12 may be left slightly loose until the handle 34 is inserted into a pocket 30, and then may be tightly secured over the upper portion of the patient 38. Generally, there is enough flexibility or pliability in the material 12 to enable the handle 34 to be positioned into a pocket 30 even after the material 12 has been secured tightly over the patient 38.

When the end of the handle 34 of the retractor 36 is inserted in a pocket 30, since the pocket 30 preferably is closed at its end opposite the open end, the retractor handle 34 is securely held in place against lateral or vertical (away from the patient) movement, thereby maintaining the retractor 36 in position to the same extent as if an assistant was holding the handle 34 firmly against the upper side of the body of the patient 38. This permits the surgeon to operate more freely in the operating field without having to avoid the hands of the assistant that otherwise would be retaining the handle 34 in position to maintain the retractor 36 at a desired location, and eliminates the need for the assistant.

The pliable material 12, the hooks 20, 22 and the pockets 30 are all intended to be manufactured at minimum cost since they are intended to be used only once during their functional life. Accordingly, an appropriate sturdy but low cost fabric or sheet material is preferably utilized to form the length of material 12 and inexpensive yet sturdy hook elements 20, 22 are secured to the material 12 in a simple and inexpensive manner to keep the cost of the assembly to a minimum. The pockets 30 may be formed by any suitable means consistent with the objective of securing the handle 34 of a retractor at a fixed location during a surgical procedure.

The location and quantity of pockets 30 along the length of material 12 may be adjusted to suit various surgical tables, patient sizes or surgical procedures. Preferably, a single universal length of material 12 with multiple open ended pockets 30 will be adjustable so as to be usable in virtually any surgical procedure involving the use of a retractor or retractor-like element that must be secured in position relative to a surgery opening or a body cavity.

A preferred embodiment of the invention has been described but it is to be understood that the invention is not to be limited to the specific embodiment but rather can be made in accordance with any means or method known to persons skilled in the art without departing from the spirit and scope of the invention.

I claim:

1. A surgical retractor holder comprising:

a length of pliable material having opposed first and second fastening end areas located along the material length;

a surgical table engaging element disposed at each of said fastening end areas;

at least one retractor handle receiving pocket connected to said material and located along the material length, said at least one pocket opening in a direction transverse to the material length;

said material length and at least one of said engaging elements being adjustably connected together so that the effective distance between the fastening end areas of the material can be varied.

2. A surgical retractor holder according to claim 1, wherein said at least one pocket is closed at one end.

3. A surgical retractor holder as claimed in claim 1, including multiple pockets disposed along the length of the material, with all of the open ends of the pockets facing in the same direction.

4. A surgical retractor holder according to claim 3, wherein said pockets are all closed at an end thereof opposite said open ends.

5. A surgical retractor holder according to claim 1, wherein the adjustable connection between said at least one table engaging element and said material length comprises a ring associated with the element and a loop of said flexible material threaded through the ring, and including a fastener for securing the material loop against reverse loosening motion through the ring after threading through thereof.

6. A surgical retractor holder according to claim 5, wherein said fastener includes a multiple loop and hook type fastener.

7. A surgical retractor holder according to claim 5, wherein said material is a fabric having a surface texture capable of functioning as a multiple loop type material of a conventional multiple loop and hook type fastener, and said fastener comprising a multiple loop type material of the type associated with such conventional multiple loop and hook type fasteners attached to the material length adjacent said one fastening end area, whereby, after threading of the loop of material through the ring, the loop type fastener material may be directly secured to the textured surface of the material to prevent reverse loosening motion of the material length.

\* \* \* \* \*